(12) United States Patent
Plath

(10) Patent No.: US 10,076,437 B2
(45) Date of Patent: Sep. 18, 2018

(54) PORTABLE AND READILY DISMANTLED HUMAN RESTRAINT SYTEM

(71) Applicant: David Plath, Schererville, IN (US)

(72) Inventor: David Plath, Schererville, IN (US)

( * ) Notice: Subject to any disclaimer, the term of this patent is extended or adjusted under 35 U.S.C. 154(b) by 610 days.

(21) Appl. No.: 13/770,074

(22) Filed: Feb. 19, 2013

(65) Prior Publication Data

US 2014/0235937 A1 Aug. 21, 2014

(51) Int. Cl.
*A61F 5/37* (2006.01)

(52) U.S. Cl.
CPC .................. *A61F 5/3761* (2013.01)

(58) Field of Classification Search
CPC ............ A63B 21/1627; A63B 21/1636; A63B 21/1645; A63B 21/1654; A63B 21/1663; A63B 21/1681; A63B 21/169; A61F 5/00; A61F 5/37; A61F 5/3715; A61F 5/3761
USPC ........ 128/846, 869, 877, 883; 482/121, 122, 482/126, 129, 131, 904; 602/32–40
See application file for complete search history.

(56) References Cited

U.S. PATENT DOCUMENTS

| | | | | |
|---|---|---|---|---|
| 680,556 A * | 8/1901 | Wieland | ........................ | 482/129 |
| 2,679,842 A | 6/1954 | Brill | | |
| 3,118,441 A * | 1/1964 | George | ........................... | 601/23 |
| 4,402,504 A * | 9/1983 | Christian | ...................... | 482/103 |
| 4,611,805 A * | 9/1986 | Franklin | ................ | A63B 21/04 |
| | | | | 482/129 |
| 5,038,799 A | 8/1991 | Fowler et al. | | |
| 5,345,947 A | 9/1994 | Fisher | | |
| 5,385,525 A * | 1/1995 | Davis | ................ | A63B 21/0552 |
| | | | | 482/121 |
| 6,015,371 A * | 1/2000 | Davitt | .......................... | 482/129 |
| 6,494,817 B2 * | 12/2002 | Lake | ............................... | 482/93 |
| 8,485,950 B2 * | 7/2013 | Adams | ......................... | 482/129 |
| 8,485,951 B1 * | 7/2013 | Adams | ......................... | 482/129 |
| 9,028,381 B2 * | 5/2015 | Mestemaker | ...... | A63B 21/0414 |
| | | | | 482/129 |
| 2010/0173759 A1 * | 7/2010 | Lalaoua | ....................... | 482/121 |
| 2011/0177921 A1 * | 7/2011 | Olson et al. | .................... | 482/92 |
| 2011/0230314 A1 * | 9/2011 | Hoffman | ............. | A63B 21/055 |
| | | | | 482/51 |
| 2014/0066267 A1 * | 3/2014 | Solah | ..................... | A63B 69/34 |
| | | | | 482/83 |
| 2014/0106948 A1 * | 4/2014 | Agostini | ...................... | 482/129 |

* cited by examiner

*Primary Examiner* — Tarla Patel

(57) ABSTRACT

A portable human restraint system is provided for use by those who practice an alternative sexual lifestyle known as dominance and submission or discipline and bondage. The restraint system includes a bondage frame that can be secured to any door of a room and easily dismantled into a compact size for storage or traveling. The bondage frame has a generally rectangular configuration formed by a top and a bottom cross member that are connected to a pair of laterally spaced vertical posts. The vertical posts are adjustable in height to allow the bondage frame to be extended if needed. A top and a bottom securement brace secure the bondage frame to the door through adjustable reduction sleeves. The reduction sleeves, being adjustable, allow the frame to be positioned further away from the door if needed. A variety of different restraining devices such as ankle and wrist cuffs can be directly or indirectly attached to various locations about the frame with the assistance of various mechanisms such as tie-down ropes and cleats, mountings rings, and spring loaded rings.

29 Claims, 6 Drawing Sheets

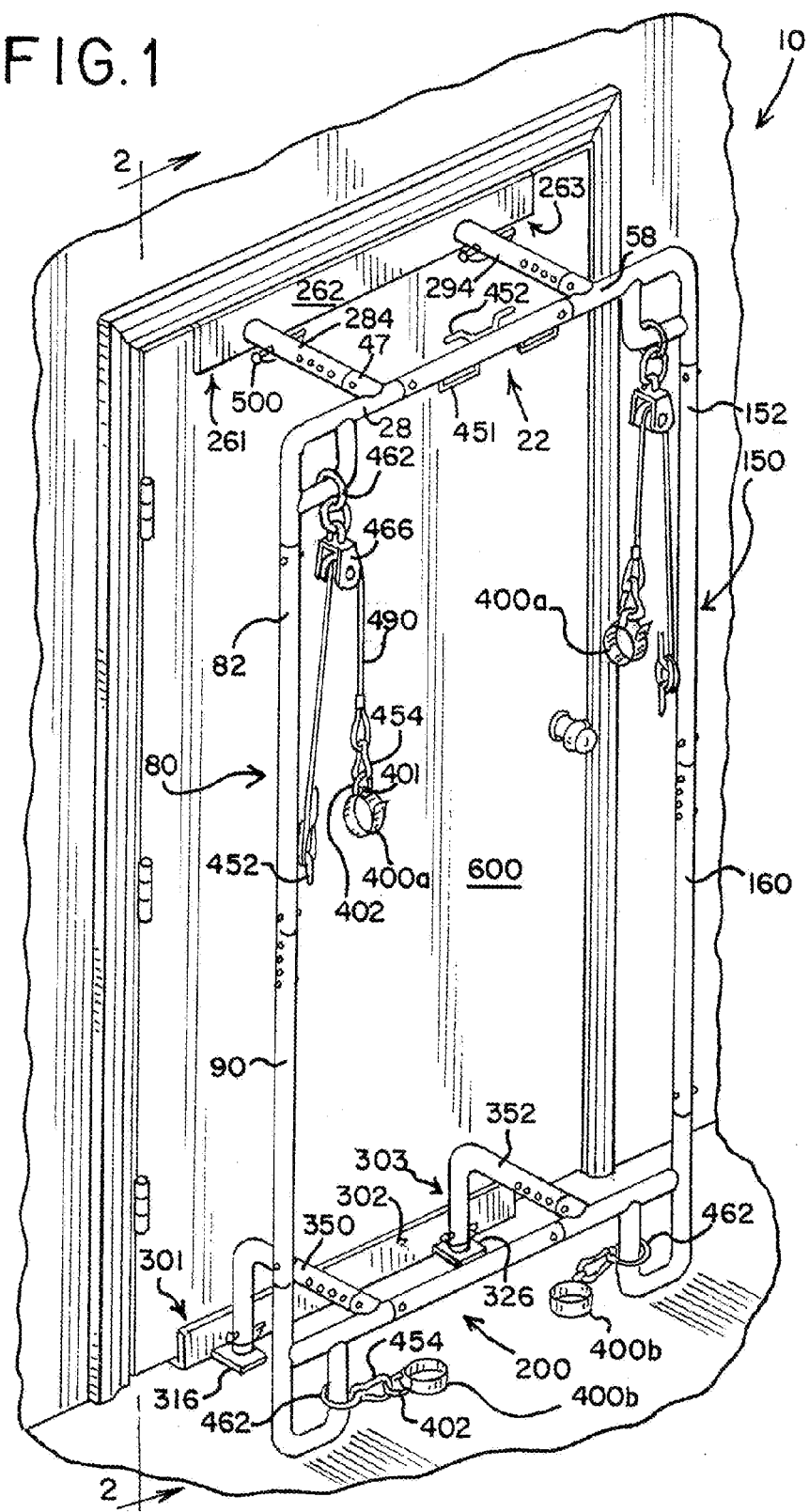

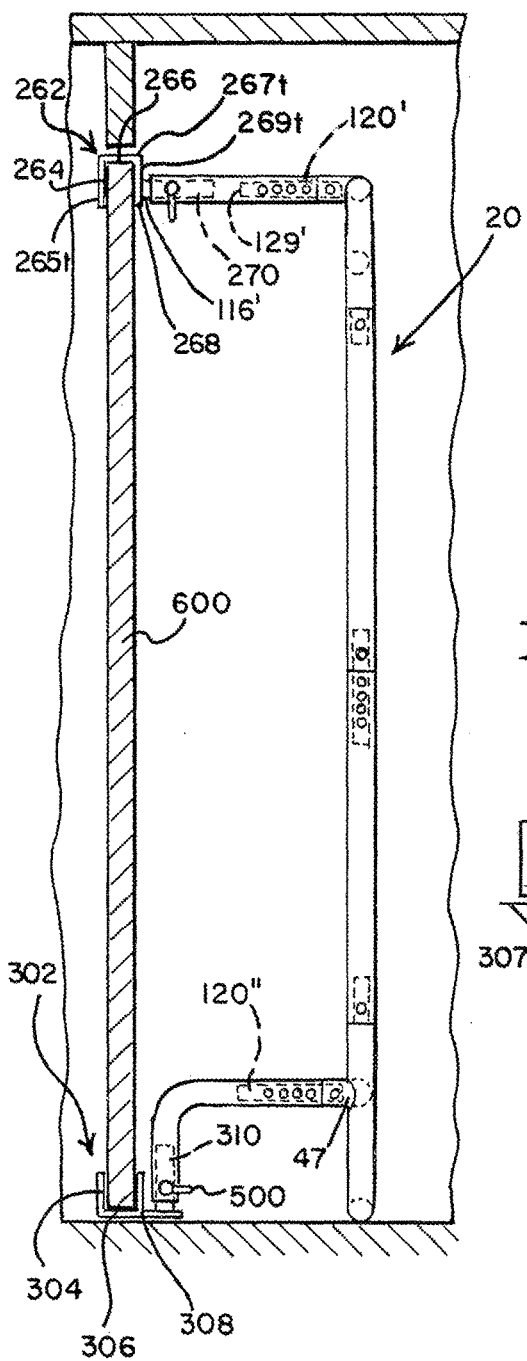
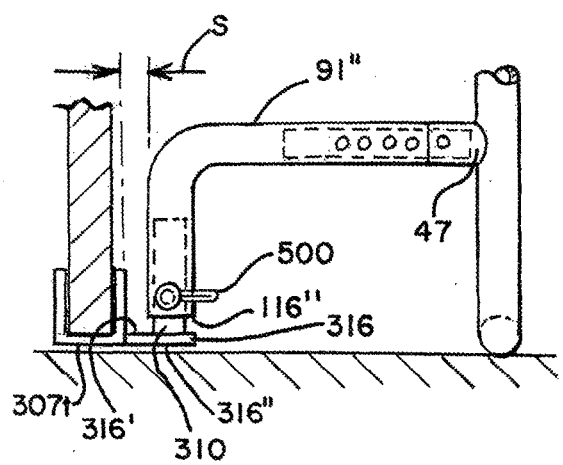

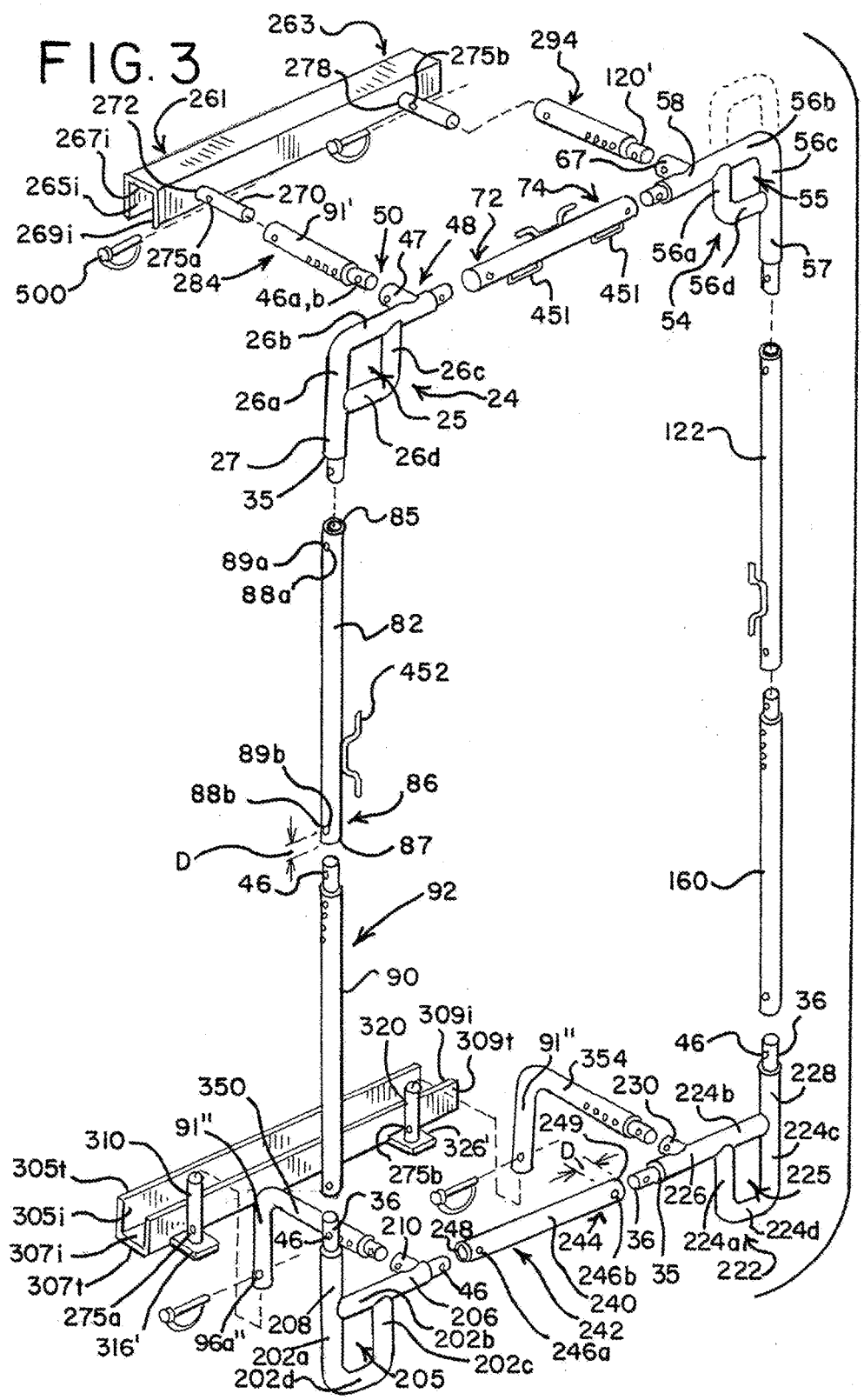

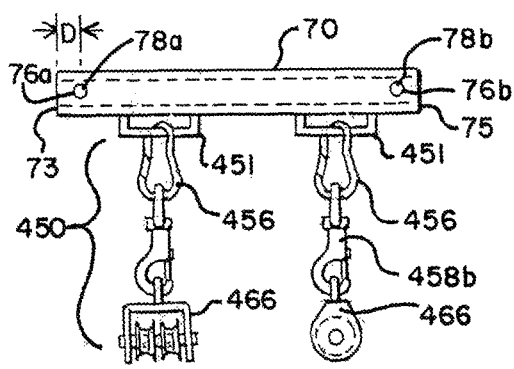
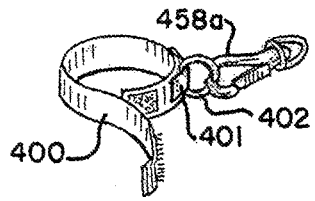
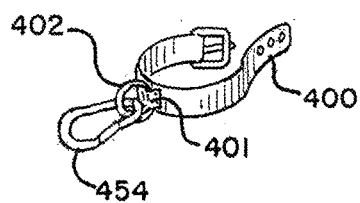
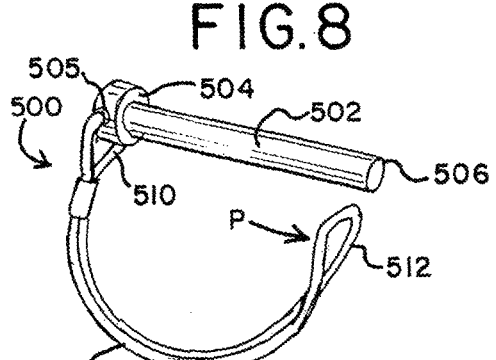
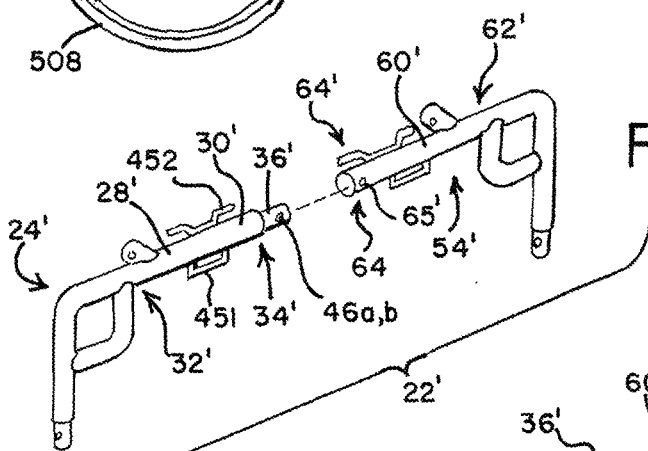
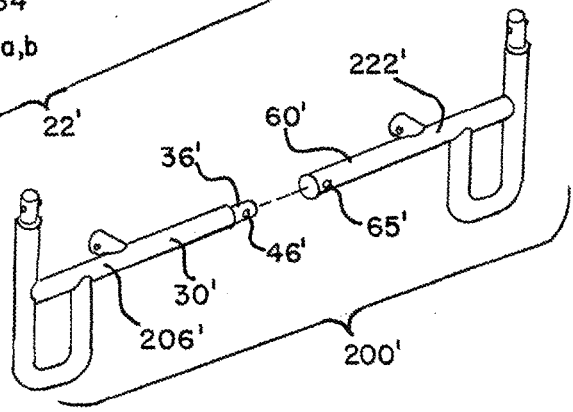

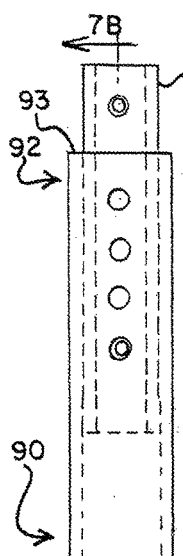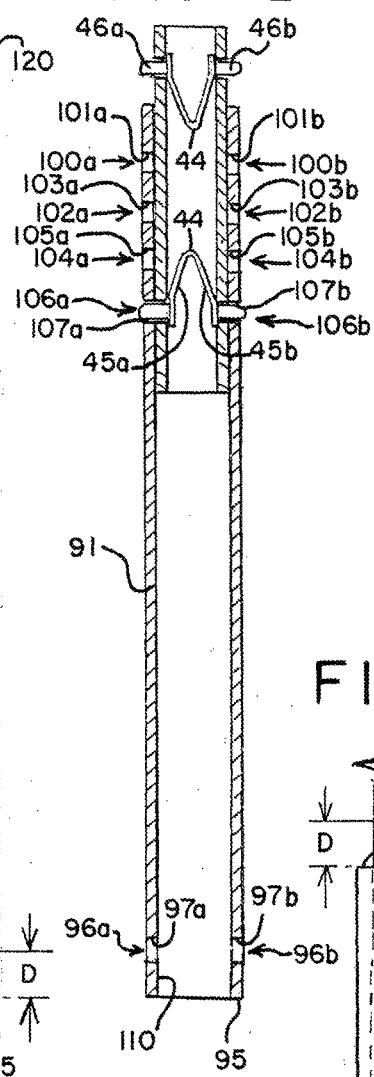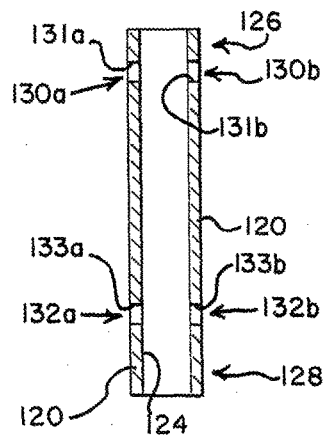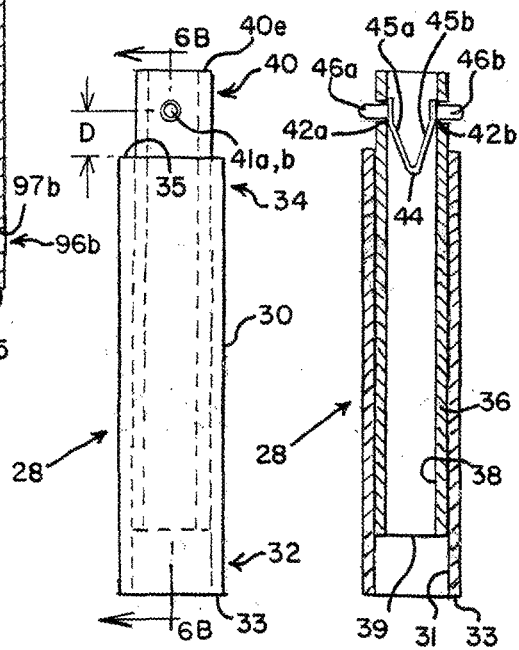

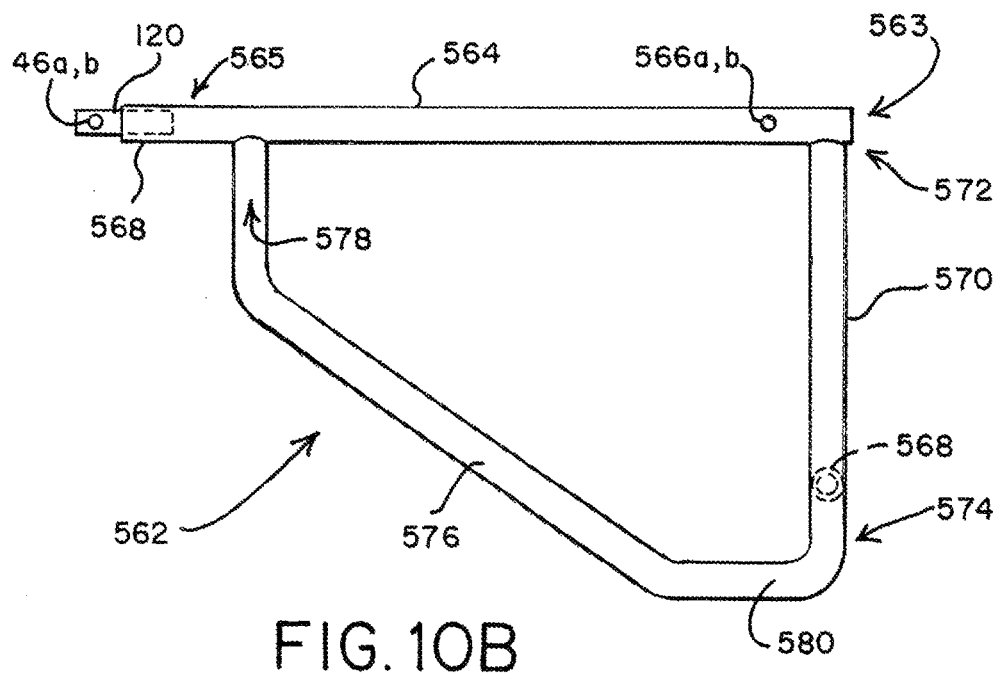
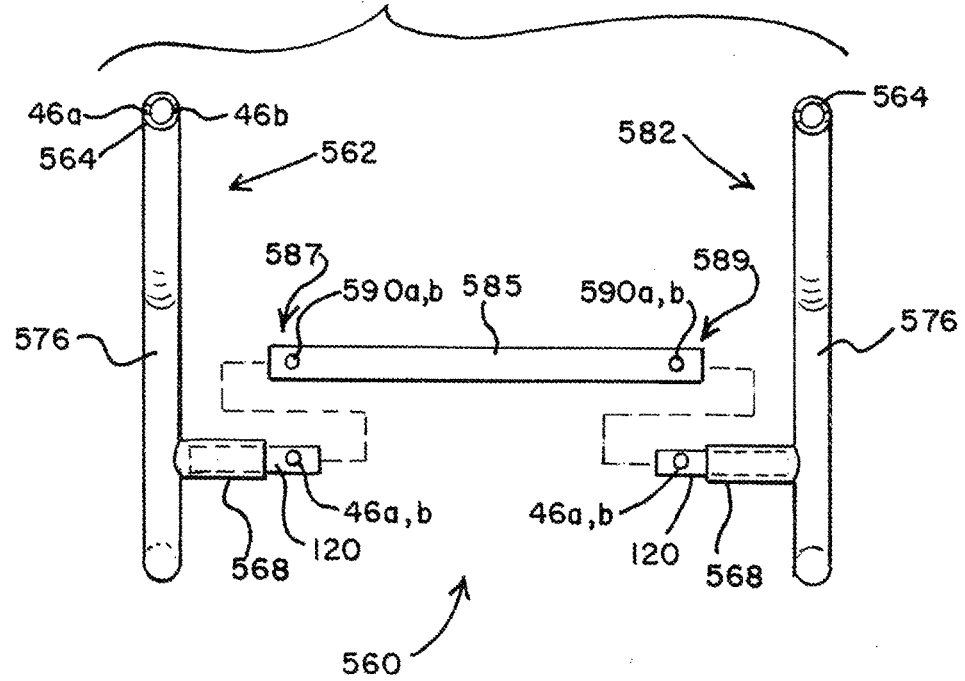

PORTABLE AND READILY DISMANTLED HUMAN RESTRAINT SYTEM

BACKGROUND OF THE INVENTION

1. Field of the Invention

The present invention relates generally to a human restraint system for use by those who practice alternative sexual lifestyles where restraint and submission is a focus of the sexual eroticism between the users of the system.

2. Discussion of the Prior Art

The prior art includes numerous types of physical restraining devices which have been previously developed for use in law enforcement, by the military and in the medical fields, including the restraint of mentally challenged individuals. U.S. Pat. No. 5,038,799, issued to Fowler et al., discloses an example of a restraint system that is intended for strict use in the medical field wherein a patient is to be tied down to a bed, yet provided limited limb movement. Informationally, this patent also discloses a plurality of several other medically-oriented restraining devices that were developed earlier to the Fowler device but had various shortfalls. U.S. Pat. No. 6,026,661, issued to Spirpoulos, discloses an example of a handcuff restraining device that was intended for use in the law enforcement field although it also had application in the military field. This patent provides an excellent background of a plurality of other law enforcement hand cuffing devices that were developed prior to the Spirpoulos device.

Despite the development of prior art restraining devices intended for specific applications, the prior art has failed to develop a restraining system that is specifically directed for use as a means to supplement those who practice alternative sexual lifestyles where bondage and restraint are the focus of the sexual eroticism between the users of the system. There is a need for a sexually-intended restraining system that can incorporate other known bondage devices such a limb restraining cuffs, bondage bars, bondage collars and belts, etc., yet provide versatility and creativity in how a person's body (slave) can be or will be restrained.

SUMMARY OF THE INVENTION

A portable human restraint system in accordance with the principals of the present invention provides a portable and readily dismantled human restraint system for use by those practicing alternative sexual lifestyles that involve dominance and submission as part of the lifestyle. A portable human restraint system in accordance with the principals of the present invention is intended for use inside a room that is provided with a door. A portable human restraint system in accordance with the principals of the present invention is comprised of a readily dismantled bondage frame which has at least one part thereof continuously resting upon the floor surface of the room and a securement means for securing the bondage frame to the top and bottom edge surfaces of the door, as well as the inside and outside faces too. A portable human restraint system in accordance with the principals of the present invention also provides a restraint adapted to selectively restrain movement of at least one part of the human body relative to the bondage frame and a plurality of restraint assistors disposed about the bondage frame. The plurality of restraint assistors are adapted to cooperate with the restrainer to assist and improve the manner in which the human body is restrained to the bondage frame.

The features and advantages of the invention will be further understood upon consideration of the following detailed description of an embodiment of the invention taken in conjunction with the drawings, in which:

BRIEF DESCRIPTION OF THE DRAWINGS

FIG. 1 is a perspective view of a first embodiment of the human restraint system of the present invention illustrating the positioning of the device within a doorway;

FIG. 2 is a cross sectional view along line 2-2 shown in FIG. 1, showing a side view of the bondage frame being anchored to a door through the securement;

FIG. 2A is a side view showing only the lowermost portion of the bondage frame shown in FIG. 2, detailing the spaced relationship between the bottom securement brace and the bottom securement arm members of the securement;

FIG. 3 is an exploded perspective view of human restraint system shown in FIG. 1;

FIG. 4 is a plan view of the upper cross link component of the top cross member of the bondage frame that is provided with two types of restraint assistors;

FIG. 5A is a perspective view of one version of a limb restraining cuff member and a first version of an attachment for securing the limb restraining cuff member to the bondage frame;

FIG. 5B is a perspective view of second version of a limb restraining cuff member and a second version of an attachment for securing the second version of the limb restraining cuff member to the bondage frame;

FIG. 6A is a plan view of a reduction sleeve component that forms a part of the bondage frame and which facilitates the connection of various bondage frame members together.

FIG. 6B is a cross sectional view taken along line 6-6 of FIG. 6A, emphasizing the relationship between the inside and outside sleeves that form the reduction sleeve shown in FIG. 6A and further emphasizing the provision of a quick snap connector within the inside sleeve;

FIG. 7A is a plan view of a tall, adjustable reduction sleeve component that forms a part of the vertical post members of the bondage frame.

FIG. 7B is a cross sectional view taken along line 7-7 of FIG. 7A, emphasizing the adjustable relationship between the inside and outside sleeves that form the tall, adjustable reduction sleeve shown in FIG. 7A and further emphasizing the provision of a quick snap connector within the inside sleeve to facilitate adjustability;

FIG. 7C is a cross sectional view of the inside sleeve being removed and isolated from the outside sleeve that was shown in FIG. 7B, said inside sleeve also shown without the inclusion of quick snap connectors;

FIG. 8 is a perspective view of a wire lock pin that is used for temporarily securing the bondage frame to the top and bottom securement braces of the securement; and FIG. 9A is an exploded perspective view of a second embodiment of the top cross member of the bondage frame.

FIG. 9B is an exploded perspective view of a second embodiment of the top cross member of the bondage frame.

FIG. 10A is a side view of a third embodiment of the top cross member of the bondage frame.

FIG. 10B is an exploded plan view of a third embodiment of the top cross member of the bondage frame shown in FIG. 10A.

DETAILED DESCRIPTION OF A PREFERRED EMBODIMENT

The present invention will now be described in detail with reference to the preferred embodiment wherein like elements will be identified by like reference numerals throughout the drawings and specification. Referring first to FIGS. 1-3, it is seen that the present invention 10 in its most versatile and readily usable embodiment is comprised of: a generally rectangularly configured bondage frame 20; a securement 260 for securing bondage frame 20 to a closed door 600; a restraint 400 for selectively and simultaneously constricting or restraining the movement of the entire human body, a particular part of the human body, or even a selected arm(s) or leg(s) to or within the bondage frame 20; and a plurality of restraint assistors 450 disposed about bondage frame 20 that cooperate with the restraint 400 to facilitate the accomplishment of a variety of selective and/or simultaneous restrained positions that are typically employed by a master upon its slave. The restraint shown in these figures are identified at 400a and 400b.

The bondage frame 20 is generally comprised of a top cross member 22 and a bottom cross member 40, each member being disposed in a parallel relationship to the other and each interconnected to a left and a right vertical post 80, 150. As seen, the posts are also disposed in a parallel relationship to the other and attached at right angles to the top and bottom members so as to give the frame its rectangular configuration. The securement 260 is generally comprised of a top securement brace 262 and a bottom securement brace 302, and a short, adjustable reduction sleeve and a modified, short adjustable reduction sleeve, each member of the securement collectively cooperating to steady the bondage frame 20 against movement through its attachment to a door of a room, identified at 600. The restraint shown in this embodiment is comprised of a plurality of identical human limb restraining cuffs 400a, 400b that may be directly or indirectly attached to bondage frame 20. Other types of restraints may be used in practicing the present invention so it should be understood that the invention is not limited to only a restraint in the form of limb restraining cuffs 400a,400b. For example, the restraint of the present invention may alternatively incorporate the use of a bondage belt, a restraining neck collar, a spreader bar(s), a restraining harness or sling or even a combination of all such restraints so as to broaden to application and use of the invention. A bondage belt and a restraining neck collar are each constructed very similarly to that of a wrist or ankle cuff, except that each of those restraints will be provided with multiplicity of attachment tabs and attachment rings incorporated into the respective devices. The restraining cuffs 400a,400b, only have a single attachment tab and attachment ring 401,402, which such attachment tabs and rings are best seen when viewing the wrist and ankle cuffs shown in FIG. 5A or 5B. With either a bondage restraining collar or a bondage belt, the general construction would be similar except that there would be a multiplicity of such attachment tab and attachment ring combinations disposed about the circumference of each of those respective devices. A spreader bar is not shown in the drawing figures because those in the art generally know that a typical one is constructed as a solid or hollow bar having a pair of limb restraining cuffs permanently attached at each distal end thereof, with a centrally located attachment means that allows the bar to be connected or attached to some other structure or restraining component. Some spreader bars may adjustable so as to allow the length of the bar to be changed as needed, depending upon its end function. The spreader bar attachment means is typically in the form of a mounting ring, much like the attachment ring 402 of a limb restraining cuff. A restraining harness or sling is also a known device that attaches about the central trunk of the body of a slave rather than to a specific body part like the cuffs or the neck collar or to a particular area of the body, like the bondage belt. The restraining harness is also provided with at least one mounting means permanently attached thereto so that the harness can be attached to some other structure or restraining component during use. Since these alternative types of restraints are well-known in the BDSM community and have similar constructions, only the limb restraining cuffs 400a,400b will be shown in the drawing figures. The present invention also anticipates the provision of a multitude of different types of restraint assistors. A combination of several restraint assistors are shown in FIG. 4 at 450, however, the invention envisions various combinations of such means, depending upon the type of restraints that are being employed and the application required by the Dom. For example, if it is desired to directly connect a chosen restraints to the bondage frame 20, then such connection may be accomplished through the provision of restraint assistors in the form of tie-down brackets 451 and/or tie-down cleats 452 (see FIG. 4), or mounting rings 462 and spring links 454 (see FIG. 1 and FIG. 5B), all depending upon the type of restraints being employed by the Dom. If indirect attachment to bondage frame 20 is desired, such attachment may be accomplished through the provision of several types of restraint assistors that may or may not be used with the tie-down cleats and brackets or mounting rings. These restraint assistors may be in the form of a single or a plurality of restraining ropes 490 that may or may not be combined rope adjustment pulleys 466 (see FIG. 1); round eye swivel tie snaps 458a (see FIG. 5A) or round eye swivel tie snaps 458b (see FIG. 4). The adjustment pulleys 466 may be of the single-spool type or they may be of the multiple-spool type so that several restraining ropes 490 may be utilized simultaneously, thereby increasing the utilization of the bondage frame 20. FIG. 4 shows a double spool type of pulley, whereas FIG. 1 shows a single spool pulley. Each type of adjustment pulley allows the Dom to introduce positional and/or tensional variations into the restraint of the limb or body part being restricted on the slave, thereby allowing the Dom to create various slave positions such as the waitress, the pit of doom, soaring, strappado, bottoms up, etc., or simply wrists offered. As FIG. 1 shows, the tie-down cleats 452 are directly attached to the bondage frame 20 at several locations about the frame so as to offer variation in the manner of restriction or the adaptability in the type of or number of restraints being employed by the Dom to create the various known slave positions. Additional tie-down cleats may be added along the frame other than at the locations shown. The mounting rings 462 are another restraint assistor that are intended to assist in achieving the various types of slave positions, whereas in some bondage positions, the mounting rings 462 are intended to have limited sliding movement along part of the bondage frame 20 in order to provide a limited degree of restrained movement relative to the bondage frame 20. The restraint shown in the drawing FIGS. 400a,400b) and the various restraint assistors and their interrelationships will be explained in greater later herein.

Pursuant to the invention as mentioned above, the bondage frame 20 in the illustrated form shown in FIG. 1 is seen to have a rectangular configuration that is defined by the interconnecting components 22, 80,150 and 200. Each of the interconnecting components is shown in the drawing figures as having a round contour, however, the invention is not to be so limited as all of the interconnecting members can be formed with any geometrically shaped contour as long as all components are constructed of the same geometric contour. For example, the frame components can be formed with squarely shaped components rather than round components. Furthermore, it is preferred that all frame components of the present invention be constructed as tubular members rather than as solid members since tubular members will facilitate ease of transportability and the rapid and expedient disassembly/reassembly of the restraint system. Moreover, it is also preferred that the various tubular framing components of the present invention be constructed of lightweight materials that provide high resistance to bending forces, such as light gage steels, aluminums or even PVC plastic.

The top component of bondage frame 20 is a referred to herein as the top cross member 22. As best seen in FIG. 3, it is comprised of a left, upper stirrup assembly 24 connected to a right, upper stirrup assembly 54 through an upper cross link 70. The left upper stirrup assembly and the right upper stirrup assembly are identical to each other and each of the stirrup assemblies include respective integrally connected stirrup segments. The stirrup segments 26a-d and 56a-d of each stirrup assembly 24,54, are identical in height and length, thereby forming respective, identical stirrup openings 25,55. As FIG. 1 shows, each stirrup opening 25,55 is provided with an identical mounting ring 462 that has a larger inner diameter relative to the diameter or cross section of the respective stirrup segments 26a-d and 56a-d. In this way, mounting ring 462 is intentionally allowed a limited amount of travel within each respective stirrup opening 25,55, through a sliding movement along the stirrup segments 26c and 26d and 56c and 56d, thereby broadening the application and use of the present invention, as will become apparent later herein once the application of the invention is explained in detail. It is also seen that the left and right upper stirrup assemblies 24,54, also include a respective left and right downward reduction sleeve 27,57, and a left and right horizontal reduction sleeve 28,58. The left and right horizontal reduction sleeves 28,58 are further provided with respective rearward-oriented stub shafts 47,67. The horizontal reduction sleeves are integrally connected to respective stirrup segments 26b and 58b, while the downward reduction sleeves 27,57 are integrally connected to respective stirrup segments 26a and 58a. There are several other locations within the bondage frame 20 that utilize these same type of reduction sleeves although in some applications, the sleeve orientation may differ, i.e., upward, downward or horizontal. Except for the horizontal reduction sleeves having the additional stub shaft component, the horizontal, upward and downward sleeves are otherwise identical to each other. Therefore, it should be understood that whenever the term "reduction sleeve" is used to describe a bondage frame component, it is referring this type of reduction sleeve. Because the horizontal reduction sleeves have an additional component that the other reduction sleeves do not have, only reduction sleeve 28 will be described in greater detail below.

Referring now to FIGS. 6A and 6B, a horizontal reduction sleeve 28 is shown in detail, but for clarity sake, the stub shaft 47 has not been included in these figures. It is seen that the reduction sleeve is actually comprised of two concentric sleeves; a first, outside sleeve 30 and a second, inside sleeve 36. The inside sleeve 36 has an outside diameter that is relatively smaller than the inside diameter of the outside sleeve to allow said sleeve 36 to slip within the inside first sleeve 30 and to be permanently attached therein against inside surface 31 by either a very tight friction fit or by gluing, heat bonding, or by other well known means. The type of permanent attachment will depend upon the type of material used in the construction of bondage frame 20. The outside sleeve 30 has a first end 32 and a second end 34, with the second end 34 defining the second end surface 35. The inside sleeve 36 also has a first end 38 and a second end 40, each of which are in positional agreement with the first and second ends 32,34, of outside sleeve 30. As best seen in drawing FIG. 6B, the second end of inside sleeve 36 is provided with a set of aligned holes 41a,41b, that respectively define the hole surfaces 42a,42b. A quick snap connector 44 is provided inside of sleeve 36 to engage within holes 41a,41b. The quick snap connector 44 is comprised of a pair of identical indexed arms 45a,45b, that are integrally connected to each other so as to give the connector spring-like characteristics that are similar to that of a bellville spring. Each arm 45a,45b includes an identical projecting tab 46a,46b that is integrally formed within each arm, near the non-connected ends thereof. The quick snap connector 44 is inserted within the hollow inside sleeve 36 and pushed towards first end 38, whereby the spring characteristics of the connector cause each arm 45a and 45b to exert pressure against the inside surface 37 of the inside sleeve 36 such that the projecting tabs 46a,46b are forced through a corresponding hole 41a,41b, into engagement with hole surfaces 42a, 42b. A substantial portion of each projecting tab extends beyond the outside surface 39 of inside sleeve 36 once the tabs are set.

As mentioned, a feature that is unique to only the horizontal reduction sleeve 28, and for that matter to all horizontally-oriented reduction sleeves that are incorporated into the bondage frame 20, is the provision of the open, tubular stub shaft 47 integrally formed into the outside sleeve 30, near the second end 34 thereof. The stub shaft 47 is disposed at a right angle to the outside sleeve 30 so as to point or project directly backwards towards the door 600 to which bondage frame 20 will be secured. The one end 48 of stub shaft 47 is integral with outside sleeve 30 while the other end 50, presents an open, female receptacle. The open female end 50 is provided with a set of aligned holes 52a,52b, (hole 52b not seen) that are respectively defined by the respective surfaces 53a,53b (surface 53b not seen). Only hole 52a and its defined surface 53a can be seen, but it should be understood that the hole 52b is diametrically disposed on the outside sleeve. The respective holes 52a,52b receive therein, the projecting tabs 46a,46b of a quick snap connector 44 that is provided within a mating component 284 of the means that secures the bondage frame 20 to door 600. The component 284 that is received within stub shaft 47 will be identified later herein below as a short, adjustable reduction sleeve, which functions to assist in attaching the left upper stirrup assembly 24 to the top securement brace 262, which in turn, is secured to door 600. The interaction between the top securement brace 262 and the stub shaft will be described later herein in conjunction with a detailed description of the securement itself.

In FIGS. 6A and 6B, it is also seen that first and second ends 38,40 of the inside sleeve are not perfectly indexed with the corresponding first and second ends of the outside sleeve 30, but rather, the first end 38 is disposed in close proximity to end 32, while second end 40 projects beyond the end surface 35. The projecting tabs 46a,46b, which assist in securing another bondage frame component to the reduction sleeve 28, are to be located the distance "D" from end surface 35 of outside sleeve 30 when inside sleeve 36 is permanently attached within outside sleeve 30. It is preferred that distance "D" be chosen in the range of 1.50 inches to 2.50 inches, said distance measured from the centerline of the holes 41a,41b, to the end surface 35. Once a distance "D" is chosen, all of the reduction sleeves that are being utilized throughout the construction of the bondage frame 20 will also be set at the same distance "D" since all are identically constructed. It necessarily follows that once the distance "D" is set, the length of the inside sleeve 36 which will be enveloped by outside sleeve 30 can then be determined. When determining that length, it is desired that the enveloped portion of inside sleeve 36 be such that the end surface 39 of the sleeve 36 be in relatively close proximity to the first end surface 33 of outside sleeve 30 after inside sleeve 36 is permanently attached to outside sleeve 30. It has been discovered that this distance should ideally be not less than 0.50 inches and no more than 1.0 inches. In that way, when this distance is kept relatively small, a substantial extent of the outside sleeve will envelope the inside sleeve, thereby increasing the overall strength of the reduction sleeve in resisting the various operating forces that are placed upon the bondage frame 20 during its use and operation. It is also intended that when a distance "D" is determined, that this same length, "D", of additional sleeve material extend above the centerline of holes 41a,41b, for two reasons. The first reason being that if the distance of the sleeve material between end surface 40e and holes 41a,41b is relatively small, the strength of second end 40 of inside sleeve 36 will be compromised. Second, it is desirable to provide this additional sleeve material above the holes 41a,41b, because this additional material will be extending further into the inside cavity of the another frame component that second end 40 mates with, thereby strengthening the connection joint against bending stresses.

Turning again to FIGS. 1 and 3, it is generally seen that the horizontal reduction sleeves 28 and 58 on each of the respective stirrup assemblies 24,54, are connected to a upper cross link member 70, respectively at a left end 72 and a right end 74 thereof. In FIG. 4, it is seen in greater detail that upper cross link 70 is a cylindrically shaped, tubular member that is provided with a set of identically sized holes 76a,76b, located an identical distance "D" from each end 72,74, with the distance "D" being the same predetermined distance that was described with respect to reduction sleeve 28. Each respective hole 76a,76b extends completely through cylindrical member 70 in a perpendicular fashion thereto such that there are actually two sets of holes in registered alignment with each other on each end. Each of the sets of holes 76a,76b so formed are defined by respective surfaces 78a, 78b, with the diameter of each hole 76a,76b being slightly larger than the diameter of projecting tabs 46a,46b on each reduction sleeve 28,58. To accomplish the connection between reduction sleeves 28,58 and upper cross link 70, each of the female open ends 72 and 74 of the upper cross link 70 are slipped over a respective inside sleeve 36 on the horizontal reduction sleeves 28,58 until the respective projecting tabs 46a,46b on each respective inside sleeve engage within the corresponding holes 76a and 76b. When the upper cross link 70 is connected as such, it should be noted that the end surfaces 73,75 of cross link 70 will come into contact against the respective end surfaces 35 of the reduction sleeves 28,58 and that there will be a deminimus amount of free space or tolerance between the outside surfaces of the projecting tabs and the respective hole surfaces 78a,78b.

Turning attention again to FIGS. 1 and 3, it is seen that the downwardly oriented reduction sleeves 27 and 57 of the left and right upper stirrup assemblies 24,54, are similarly connected to respective top sections 82,122 of the left and right cylindrical vertical posts 80,150. Each vertical post 80,150, is comprised of a cylindrically shaped, tubular top sections 82,152 connected to a bottom sections 90,160, with the respective bottom sections being comprised of an adjustable reduction sleeve. Since each vertical post is structurally and functionally identical to the other, only the left vertical post 80 will be described in greater detail. The top section 82 is a hollow tube having an open top end 84 and an open bottom end 86, each end defining respective end surfaces 85,87. Each end 84,86 is provided with a set of identically sized holes 88a,88b, located an identical distance "D" from each end surface 85,87. The distance "D" is the same distance that was previously described. Each respective hole 88a,88b extends completely through the cylindrical top section member 82 in a perpendicular fashion thereto such that there are actually two holes 88a,88b in registered alignment with each other on each end 84, although only one of the holes can be seen in the figures. Each hole 88a,88b so formed is defined by a respective surface 89a,89b, with the diameter of each hole 88a,88b being slightly larger than the diameter of projecting tabs 46a,46b that will be engaged within the holes. To connect the downward oriented reduction sleeve 27 to the top section 82 of vertical post 80, the female open end 84 is slipped over the inside sleeve 36 on the downward reduction sleeve 27 until the projecting tabs 46a,46b of inside sleeve are fully engaged within the corresponding holes 88a, thereby connecting the top section 82 to the left upper stirrup assembly 24. The downward oriented reduction sleeve 57 on the right upper stirrup assembly 54 would be connected to the top section 152 of right vertical post 150 in exactly the same manner. When the connection is completed, the top end surface 85 will come into resting contact against the surface 35 on the downward oriented reduction sleeve 27, with a deminimus amount of tolerance therebetween. The bottom end 86 of top section 82 connects to the top end 92 of bottom section 90 through a similar interaction between the holes 88b and the projecting tabs 46 that are associated with the bottom section member 90. As mentioned above, the bottom section 90 of vertical post 80 is comprised of an adjustable reduction sleeve. This adjustable reduction sleeve is structurally similar to the reduction sleeve 28 previously described in that it too is comprised of two concentric sleeves, except that the inside sleeve 120 is allowed to move relative to the outside sleeve 91 such that the overall length can be extended. This tall, adjustable reduction sleeve can also be removed from the lower stirrup assembly 202, which is unlike a static reduction sleeve such as the horizontal reduction sleeve 28, where that inside sleeve 36 could not move since it was permanently attached to its outside sleeve 30 and since the outside sleeve 30 was integrally attached to one of the segments of the stirrup assembly.

The tall, adjustable reduction sleeve is shown in greater detail in FIGS. 7A-7C. There, it is seen that the tall, adjustable and removable reduction sleeve is comprised of two concentric sleeves; a first, outside sleeve 91 and a second, inside sleeve 120. The inside sleeve 120 has an outside diameter that is slightly smaller relative to the inside diameter of the outside sleeve 91, thereby allowing inside sleeve 120 to frictionally slide along the inside surface 110 of the outside sleeve 91. The outside sleeve 91 has a top end 92 and an open bottom end 94, with the top end 92 defining the end surface 93 and the bottom end 94 defining end surface 95. The figures also show that the bottom end 94 is provided with a hole 96 that is located a distance "D" from bottom end surface 95. Hole 96 extends completely through the cylindrical bottom section member 90 in a perpendicular fashion thereto, thereby forming two holes 96a,96b, that are in registered alignment with each other. Each hole 96a,96b so formed is delimited by a respective surface 97a,97b, with the diameter of each hole being slightly larger than the diameter of projecting tabs 46a,46b that will be received therein once the bottom end 94 is connected to another member. The holes 96a,96b receive therein the projecting tabs 46a,46b that are located on the upward oriented reduction sleeve 208 of bottom left stirrup assembly 202 (See FIG. 3) when the bottom end 94 of post 80 is releasably connected to the bottom member 200 of the bondage frame 20. This connection will be explained later below when the bottom member 200 is described in detail.

The top end 92 of the outside sleeve 91 is provided with a series of vertically aligned throughbores 100-106, each throughbore extending entirely through the outside sleeve 91 in a perpendicular fashion thereto, thereby forming respective pairs of throughbores 100a,100b, 102a,102b, 104a,104b and 106a,106b, whereby each throughbore hole that forms the pair, i.e., 100a,100b, 102a,102b, etc., is in registered alignment with the other throughbore of that pair. Each pair of throughbores 100a,100b-106a,106b so formed are delimited by a respective throughbore surfaces 101a,101b,103a, 103b,105a,105b and 107a,107b. Moreover, each of the throughbores 100-106 are equidistantly spaced apart in the vertical direction from the other.

The movable inside sleeve 120 that is received within outside sleeve 91 has a first end 126 and a second end 128, each of which are in positional agreement with the first and second ends 92,94 of outside sleeve 91, with first end 92 projecting beyond the top end surface 114 of outside sleeve 91. As best seen in drawing FIG. 7C, the first end 126 of inside sleeve 120 is provided with a set of aligned holes 130a,130b, that respectively define the hole surfaces 131a, 131b, while the second end 128 is provided with a set of aligned holes 132a,132b that define the hole surfaces 133a, 133b. Each of the sets of holes 130a,130b and 132a,132b are provided to receive a quick snap connector 44 of the type that was previously described in detail above. A respective quick snap connector 44 is initially inserted within each respective open end of the hollow inside sleeve 120 and then slid into the positions that are shown in the drawing figures. When the quick snap connectors are initially being slid down each end of the inside sleeve 120, the spring characteristics of the connector cause each respective arm 45a and 45b to exert pressure against the inside surface 124 of the inside sleeve 120 such that when the quick snap connectors encounter a hole, the projecting tabs 46a,46b on each quick snap connector 44 are forced into a respective and corresponding hole 130a,130b and 132a,132b. By that it is meant that for the uppermost quick snap connector 44, projecting tab 46a will engage hole 130a, while projecting tab 46b will engage hole 130b. Likewise, with the lowermost quick snap connector 44, the projecting tab 46a will encounter hole 132a and the projecting tab 46b will encounter hole 132b. Once the respective projecting tabs are engaged within the respective holes as mentioned, it is seen that a substantial portion of each projecting tab extends beyond the outside surface 122 of inside sleeve 120. In FIG. 7B, it is also seen that the centerline of holes 130a,130b, and necessarily the centerline of the projecting tabs 46a,46b on the upper quick snap connector 44, once engaged therein, are located a distance "D" from the top end surface 126. FIG. 7B also shows that the projecting tabs 46a,46b on the lowermost quick snap connector 44 extend well beyond outside surface 122 so as to project into and completely through the lowermost throughbores 106a and 106b on outside sleeve 91 and even slightly beyond the outside surface 122 of outside sleeve 91. In FIG. 7B, the inside sleeve 120 is shown to be locked into the lowest position possible as the projecting tabs are engaged within the lowermost throughbores 106a, 106b. With any quick snap connector 44 that is utilized within the invention, it is intended that the projecting tabs 46a,46b, extend beyond the surface of a particular outside sleeve so that a user of the system can readily access the projecting tabs so that the tabs can be depressed inwardly towards each other in order to release the tabs from engagement with the hole surfaces, thereby facilitating the extension or compression of the vertical height of the bondage frame 20. The ability to change the vertical height of bondage frame 20 is important to the effective operation of the invention because not all door heights are the same, so the ability of the bondage frame 20 to adapt to the environment is desirable. Based upon the vertical height of the door being encountered, the user of the invention would determine which throughbore hole sets 100-106, best suits his application. If it is determined that the vertical height of the bondage frame 20 requires extending, then the vertical height of the left vertical post 80 can be readily and quickly extended by pulling the inside sleeve 120 out of the outside sleeve 91 until the tabs engage with a higher-positioned throughbore, and if it is desired to reduce the vertical height of the bondage frame, then the vertical height of the left vertical post can be compressed by pushing the inside sleeve 120 downwardly into the outside sleeve 91 until the projecting tabs engage a desired lower-positioned throughbore. Movement in either direction is readily accomplished by simultaneously depressing each of the projecting tabs 46a, 46b inwardly towards each other to the point where the inherent spring pressure being exerted by each arm 45a,45b is overcome such that the tabs disengage from engagement with throughbores 100a,b-106a,b, whereby inside sleeve 120 is now free to be moved in either direction. In the case of the tabs being engaged within the lower most throughbores 106a,106b and a desire to extend the vertical height of frame 20, the inside sleeve 120 would be pulled upwardly and outwardly from outside sleeve 91 until the projecting tabs 46a,46b are aligned with and allowed to reengage themselves within one of the other throughbore hole sets 104a,104b, 102a,102b or 100a,100b that are vertically disposed above throughbores 106a,106b. To compress the height, the projecting tabs 46a,46b would likewise be released as described above, with the inside sleeve 120 being pushed downwardly into the outside sleeve 91, until a desired, lower throughbore hole set is engaged. In this way, the vertical height or extent of the left vertical post 80 can be lengthened or shortened to the degree determined by the number of throughbore holes that were provided on the outside sleeve and by the physical spacing or the distance between each of the throughbores. It was discovered that if the bondage frame 20 is provided with more than six inches (6.0") of extension capability, the integrity of the bondage frame can become compromised. Therefore, it is desirable to construct the components of bondage frame 20 such that when the vertical posts are in their most-compacted positions, the vertical height of bondage frame is about 79 inches, measured from the floor to the highest point on top cross member 22. This desired vertical frame height is designed to best accommodate a standard door height of 80 inches, with the inherent capability to accommodate non-standard door heights that fall between 80-86 inches without compromising the integrity of the bondage frame.

To connect the bottom section 90 of the left vertical post 80 to the bottom member 200, and specifically to the lower left stirrup assembly 202, the open bottom end 94 of bottom section 90 is slipped over the inside sleeve 36 of the upwardly projecting reduction sleeve 208 on the lower left stirrup assembly until the projecting tabs 46 of inside sleeve 36 engage within holes 96a,96b. The upwardly projecting reduction sleeve 226 on the lower right stirrup assembly would be connected to the bottom section 160 on the right vertical post 150 in exactly the same manner. Again, there will be a deminimus amount of free space or tolerance between the outside surfaces of the projecting tabs and the respective surfaces 97a, 97b to allow the projecting tabs to be readily released from engagement when it is desired to disassemble the entire bondage frame.

Like the top cross member of bondage frame 20, a bottom cross member 200 of the frame is connected to the left vertical post 80 and the right vertical post 150. Bottom cross member 200 is similarly comprised of a lower left stirrup assembly 202 connected to a lower right stirrup assembly 222 through the lower cross link 240. The lower left stirrup assembly and the lower right stirrup assemblies are identical to each other and each of the stirrup assemblies include respective integrally connected stirrup segments. The stirrup segments 202a,202c and 224a,224c on stirrup assembly 202,222, are identical in length, however, those segments are relatively longer than the stirrup segments 202b,202d and 224b,224d, which are identical in length to each other. Because those two segments are longer than the other segments, the respective stirrup assembly segments collectively form a rectangularly-shaped stirrup opening 205 and 225. The stirrup assemblies 202,222 are intentionally designed to rest upon the floor surface in order to provide additional strength and stability to the bondage frame 20. These stirrup assemblies are also intentionally designed into the frame structure so as to provide another location on the frame where a slave can be restrained. If the bondage frame did not incorporate the lower stirrup assemblies, the entire lower end of the frame would have to rest upon the floor, leaving a Dom without the availability of having a lower part of the bondage frame for attaching his slave thereto. By way of illustration, provision is made for restraining a slave at the bottom of the bondage frame by providing each stirrup opening 205,225 with an identical restraint assistors in the form of a mounting ring 462. Each mounting ring is identical and has a larger inner diameter relative to the diameter or cross section of the respective stirrup segments. Since the respective segments 202d and 224d rest upon the floor surface of the room, each of the mounting rings 462 will have a limited capacity to travel or move within each respective stirrup opening 205,225, that being along the respective segments 202c, 224c. Nevertheless, even with limited travel capacity, FIG. 1 shows that ankle restraining cuffs can present a Dom with another point of enslavement to the bondage frame 20.

As FIGS. 1 and 3 further illustrate, the lower left and lower right stirrup assemblies 202,222, are also comprised of respective left and right horizontal reduction sleeves 206,226 and left and right upward reduction sleeves 208, 228, with each of the horizontal reduction sleeves including rearward-facing stub shafts 210,230. Each respective stub shaft is integrally formed into an outside sleeve of the respective horizontal reduction sleeves. The horizontal and upward reduction sleeves 206,226 and 208,228, are comprised of identical components and function exactly like the horizontal and downward reduction sleeves that were previously described in greater detail earlier herein with respect to the top cross member, therefore, they will not be described in any further detail.

From the foregoing, it is seen that the horizontal reduction sleeves 206 and 226 are connected to a cylindrically shaped, tubular lower cross link member 240, respectively at a left end 242 and a right end 244 thereof. The tubular lower cross link member 240 is identical to the upper cross link member 70 that was previously described above and shown in FIG. 4, except that lower cross link member 240 does not include any restraint assistors (components 451,452 on member 70). The lower cross link member 240 is provided with a set of identically-sized hole sets 246a,246b, that are located an identical distance "D" from each end 242,244, with each hole of a set being in registered alignment to the other. Each of the sets of holes 246a,246b has a diameter that is slightly larger than the diameter of projecting tabs 46 that are provided on the horizontal reduction sleeves 206,226. Connecting the horizontal reduction sleeves 206,226 to the lower cross link member 240 is accomplished by sliding each of the open ends 242 and 244 over a respective inside sleeve 36 on each of the reduction sleeves 206,226, until the projecting tabs 46 of each inside sleeve engage within the corresponding holes 246a and 246b. As previously described, when the projecting tabs 46 are engaged within holes 246a,246b, the respective end surfaces 248,249 of cross link member 240 will come into contact against the respective end surfaces 35 of the reduction sleeves 206,226. To disassemble the lower cross link member 240 from the lower left and right stirrup assemblies 202,222, one set of the projecting tabs that are engaged within holes 246a or 246b would be chosen for manipulation, whereby those projecting tabs would be simultaneously depressed towards each other to the point where the tabs disengage from the holes, thereby allowing that end of the lower cross link member 240 to be separated from inside sleeve 36 of the horizontal reduction sleeve, 206 or 226, depending upon which end is first manipulated. The same process would then be performed on the opposite end of the lower cross link member.

Another embodiment of the bondage frame 20 of the invention is possible through a modification of the top and bottom cross members, whereby FIG. 9A illustrates the modified top cross member and FIG. 9B illustrates the modified bottom cross member. Turning attention first to FIG. 9A, the modified top cross member is now identified as element 22', and it is seen that the upper cross link 70 member has been eliminated such that the upper left stirrup assembly 24' is directly connected to the upper right stirrup assembly 54'. It can be appreciated from comparing the left upper stirrup assembly 24' in this illustration to the left upper stirrup assembly 24 shown in FIG. 3, that left upper stirrup assembly 24' in FIG. 9A includes a horizontal reduction sleeve 28' that has a significantly longer outside sleeve 30'. In all other respects, reduction sleeve 28' is the same as horizontal reduction sleeve 28 that was previously described. When comparing the right upper stirrup assembly 54' to the same stirrup assembly 54 in FIG. 3, it is seen that instead of being provided with the horizontal reduction sleeve 58, stirrup assembly 54' instead is provided with an extended tubular sleeve 60' that has a first end 62' that is integral with the stirrup assembly 54' and a second end 64' that presents as an open, female receptacle for receiving therein, the inside sleeve 36' of the horizontal reduction sleeve 28'. Projecting tabs 46a' and 46b' on the horizontal reduction sleeve 28' engage within the aligned throughbores 65' on the second end 64' of tubular sleeve 60'. The outside sleeve 30' is also provided with a restraint assistors in the form of a tie-down bracket 451 and a tie-down cleat 452, both disposed near the second end 34', while the tubular sleeve 60' is provided with an identical tie-down bracket and tie-down cleat near second end 64'.

Because upper cross link 70 of top cross member 22 was essentially identical to the lower cross link 240 of bottom cross member 200, the lower cross link member was also eliminated as just described with the upper cross member, this modified bottom cross member 200' shown in FIG. 9B. Like the modified top cross member shown in FIG. 9A, the lower left stirrup assembly 202' now includes a horizontal reduction sleeve 206' that has a significantly longer outside sleeve 30'. The lower right stirrup assembly 222' is now provided with an extended tubular sleeve 60' that has one end integral with the lower right stirrup assembly 222' and the other end presenting an open, female receptacle for receiving the inside sleeve 36' of the horizontal reduction sleeve 206' on the lower left stirrup assembly 202'. The inside sleeve 36' of the horizontal reduction sleeve 206' is provided with projecting tabs 46a' and 46b' that engage within the aligned throughbores 65' on the second end of the tubular sleeve 60' when the lower left and lower right stirrup assemblies are joined together.

With bondage frame 20 having been thoroughly described in detail, it is necessary to describe and understand how the frame is secured to a door so that it can be readily transported and utilized. As FIGS. 1, 2, and 3 best emphasize, bondage frame 20 is temporarily secured to a door 600 through a securement that is partially comprised of a top securement brace 262 and a bottom securement brace 302, each brace being identical in length and structure. The top securement brace 262 is comprised of a distal web 264, and intermediate web 266 and a proximate web 268, each web integrally connected together to form a U-shaped channel. The distal web has an inside surface 265i and an outside surface 265t, while the intermediate web has an inside surface 267i and an outside surface 267t and the proximate web has an inside surface 269i and an outside surface 269t. Likewise, the bottom securement brace 302 is comprised of a distal web 304, and intermediate web 306 and a proximate web 308, each web integrally connected together to also form a U-shaped channel. The distal web of the bottom brace has an inside surface 305i and an outside surface 305t, while this intermediate web has an inside surface 307i and an outside surface 307t, and the proximate web has an inside surface 309i and an outside surface 309t. The top securement brace 262 is further provided with a left securement arm 270 and a right securement arm 276, each arm permanently attached to outside surface 269t of proximate web 268 near a respective left end 261 and a right end 263 thereof. Each of the securement arms 270 and 276 are identical to the other, with each securement arm having an open, tubular construction, although these arms can be made as a solid bar. A respective base end 272,278, on each arm is provided with a set of holes 275a,275b that are identical in size to the other and which extend through the open tube in registered agreement. The respective holes 275a,275b receive identical wire lock pins 500. Each wire lock pin 500 offers an expeditious means for firmly fixing the assemble bondage frame to the top and bottom securement braces 262,302 of the securement 260. Turning attention to FIG. 8, it is seen that each wire lock pin 500 is comprised of a tang 502 and a locking band 508. The tang 502 has a first end comprising a head 504 and a second end comprising a tip 506. The head includes a hole 505 that extends completely therethrough. The locking band 508 has a first end 510 that is secured within hole 505, and a second open 512 for capturing the tip end of tang 502. The locking band 508 is capable of pivoting relative to the tang 502. In this way, the locking band 508 is first directed away from tang 502 in order to allow the insertion of the tang within holes 275a, 275b without interference from the locking band. After the head 504 is fully seated against outside sleeve of the short, adjustable reduction sleeve, then locking band 508 is re-directed towards tang 502. To lock tang 502 firmly in place, the open capturing end 512 must slipped over the tip end 506 of tang 502. Locking band 508 has a very resistant, inherent spring capacity and that spring capacity must be overcome prior to open capturing end 512 being slipped over tip end 506. This is done by continuously providing a pulling force on the open capturing end 512 in the direction "P" and simultaneously pivoting the locking band within head 504 until the open capturing end is perfectly aligned with the tip end 506. When so aligned, the pulling force is released, whereby the open capturing end 512 of locking band 508 will move back towards head 504, thereby enveloping tip end 506. In order for the tang 502 to be pulled from engagement with holes 275a,275b, the locking band 508 must be pulled in an opposite direction to "P" and then disengaged with tip end 506 before swinging locking band away from tang 502. Because the inherent spring characteristics of locking band 508 are rather stout, the wire lock pin 500 provides an excellent means of ensuring that the pinned connection is guaranteed and it provides the advantage that all the pieces of the locking mechanism are held together as one piece. For example, if a standard clevis pin was provided in place of the wire lock pin 500, the clevis pin would require a pin for insertion into a hole provided in one end of the clevis tang, leaving the opportunity for that pin to get lost whenever the system is dismantled and transported somewhere else. Likewise, if a standard nut and bolt were substituted for the wire lock pin 500, it would be very easy to lose the nut. In either case, if one of the components were lost, the integrity of this connection would not be guaranteed as when a wire lock pin 500 is provided.

Turing attention again to FIGS. 1 and 3, it is seen that the bottom securement brace 302 is provided with a left stanchion plate 316 and a right stanchion plate 326, each of which are permanently attached to outside surface 309t of proximate web 308 near a respective left end 301 and a right end 303 of the securement brace 302. As best understood when viewing FIG. 2, the bottom surface 316" of stanchion plate is co-planar with the outside surface 307t of intermediate web 306. Stanchion plate 326 is similarly attached to intermediate web 306. As best seen in FIG. 3, the left and right stanchion plates 316 and 326 are provided with respective stanchions 310, 320 permanently attached thereto. The left and right stanchion plates and left and right stanchions are identical to each other, with the stanchions having an open, tubular construction of the same length. Each stanchion has a respective base end 272,278, which includes an identically-sized and registered holes 275a,275b extending therethrough. The respective holes 275a,275b on each stanchion also receive the same wire lock pins 500 that were used in securing the top securement brace to the short, adjustable reduction sleeves.

As best seen when viewing FIG. 1, the top and bottom securement braces 262,302, are intentionally sized to have a length or extent that is slightly shorter than the average width of door 600, which is typically 32 inches. At this length, the securement braces will not impede an easy opening and closing of the door 600, which is important in the function of readily assembling and dissembling the bondage frame 20. Because some doors are only 24 inches wide, the securement braces 262,302 in that specific application would not work, but rather a second set of securement braces would have to be used, with those braces being made slightly shorter than 24 inches long. Even when when securement braces 262,302 are constructed to be slightly shorter than 32 inches long, it has been found that they will adequately accommodate a 36" wide door. As seen in FIG. 1, the securement arms 270,276 and the stanchions 310,320 are respectfully located inward from the absolute ends of the top and bottom securement braces so that the bondage frame 20 will not be secured exactly at the corners of the bondage frame. This offset is intentional because when the bondage frame 20 is secured at these locations instead of at the corners, the strength of the bondage frame 20 will be increased so as to better resist bending stresses that occur at the vertical and horizontal center points of bondage frame 20. As FIG. 1 also shows, it is preferable that the top and bottom members 22,200 and the left and right vertical posts, 80, 150, be collectively dimensioned such that a fully assembled bondage frame 20 will have a lateral width and a vertical height that approximates that of a standard door, which is 32 inches wide, and 80 inches tall. Recall that the vertical height of each vertical post can be adjusted to allow an additional six inches of extension, therefore, when a taller-than-standard door height is encountered, the bondage frame 20 can readily be extended from its lowest, most compacted position, to that of the taller door height.

The securement further includes another component that interfaces and connects the top and bottom securement braces 262,302 to the bondage frame 20. In FIG. 3, it is seen that the left and right short, adjustable reduction sleeves 284,294, are interconnected between the securement arms 270,276, and the upper left and upper right stirrup assemblies 24,54. The left and right short, adjustable reduction sleeves 284,294 are identical to the other and function exactly like the tall, adjustable reduction sleeves that were previously described above with respect to the bottom sections of the left and right vertical posts. The only physical difference between the short and the tall adjustable reduction sleeves is the length of the respective outside sleeves. Because the structural components of the tall and short sleeves are identical, the nomenclature used to identify the components of the tall, adjustable reduction sleeve will be used to describe the short, adjustable reduction sleeve and only the short, reduction sleeve on the left side will be described in further detail. The short, adjustable reduction sleeve 284 is connected to the securement arm 270 on its one end and to the stub shaft 47 on its other end. As described earlier herein, all stub shafts 47 are provided with holes 52a,52b. The projecting tabs 46a,46b that are provided on inside sleeve 120' of the short, adjustable reduction sleeve 284, engage within holes 52a,52b so as to secure that end of short, adjustable reduction sleeve 284 to the upper left stirrup assembly 24. The other end of short, adjustable reduction sleeve 284 is connected to the top securement brace 262 by sliding the outside sleeve 91' over the securement arm 270 until bottom end surface 116' of outside sleeve 91' is in contact against surface 269t of proximate web 268. FIG. 2 intentionally does not show these surfaces to be in contact against each other for the sake of clarity purposes. When in this attached position, the first end of securement arm 270 extends inside the outside sleeve 91' such that it will nearly be abutting the bottom end surface 129' of inside sleeve 120', as best seen in FIG. 2. Just like the tall, adjustable reduction sleeve, the inside sleeve 120' of the short adjustable adjustment sleeve is capable of movement relative to outside sleeve 91' so that the length or extent of the short adjustable reduction sleeve 284 can be increased or decreased as desired by adjusting the lowermost quick snap connector along the series of throughbores formed in the outside sleeve. For the sake of brevity, reference to FIGS. 7A-7C and the description of how to extend the inner sleeve of the tall, adjustable reduction sleeve should be made as that description will be the same for extending the short, adjustable reduction sleeve. By increasing the length of the short adjustable reduction sleeve 284, the bondage frame 20 can be moved further away from the door 600 if desired.

The securement is further comprised of a similar bottom component that interfaces and connects the bottom securement brace 302 to the bondage frame 20. In FIGS. 1-3, it is seen that the left and right stanchions 310,320 of bottom securement brace 302 are respectively connected to the lower left and lower right stirrup assemblies 202,222 through a left side and a right side modified, short adjustable reduction sleeve 350,352. Each of these adjustable reduction sleeves are identical to the other, therefore, only the left sleeve will be described. Each modified, short adjustable reduction sleeve 350,352 functions exactly like the short, adjustable reduction sleeve 284 that was described immediately above. The only physical difference between the modified, short adjustable reduction sleeve 350 and the short, adjustable reduction sleeve 284 is in the construction of the respective outside sleeve components. In drawing FIGS. 1-3, it is seen that the outside sleeves 91" on the modified, short adjustable reduction sleeves 350,354 terminate with a 90 degree bent end, thereby giving the outside sleeves 91" an L-shaped profile. In FIGS. 2 and 2A, it is further seen that when the modified, short adjustable reduction sleeves are attached to the stub shafts 47 of the lower stirrup assemblies, the modified, short, adjustable reduction sleeves are shorter than the short, adjustable reduction sleeves, assuming of course that the respective inside sleeves 120' and 120" are set at corresponding adjustment throughbores. In FIG. 2A, this difference in length is seen to be the distance represented by the space between proximate web outside surface 309t and the outside surface of the outside sleeve 91", represented as the distance "S". In all other respects, the remaining components comprising the modified, short reduction sleeve 350 are the same as those of the short, adjustable reduction sleeve 284. In FIGS. 2 and 2A, the modified short adjustable sleeve 350 on the left side of the bottom securement brace 302 is being shown in detail where it is seen that one end of the modified, short, adjustable reduction sleeve 350 is connected to the left stanchion 310, while the other end is connected to the stub shaft 47. As described earlier herein, stub shaft 47 is provided with a set of holes 52a,52b that are defined by the surfaces 53a,53b. The uppermost projecting tabs 46 that are provided on inside sleeve 120" engage within holes 52 so as to secure that end of the modified, short adjustable reduction sleeve 350 to the lower left stirrup assembly 224. The other end of the modified, short adjustable reduction sleeve 350 is connected to the bottom securement brace 302 by sliding the L-shaped end of outside sleeve 91" over the stanchion 310 until bottom end surface 116" of outside sleeve 91" is in contact against the top surface 316' of stanchion plate 316. FIG. 2A intentionally does not show the two surfaces in contact with each other for the sake of clarity purposes in identifying the elements involved. When in this position, the hole 96a" formed on outside sleeve 91" is aligned with hole 308 formed in stanchion 310, which in turn, is aligned with hole 96b" (not seen) on the backside of outside sleeve 91". With all the holes in alignment, a locking pin 500 that was previously described, is used to secure the modified short reduction sleeve to the bottom securement brace 302. Just like the short, adjustable reduction sleeve, the inside sleeve 120" of the modified, short adjustable adjustment sleeve is capable of movement relative to outside sleeve 91" so that the length or extent of the sleeve can be increased. By increasing the length of the modified, short adjustable reduction sleeve, the bondage frame 20 can be moved further away from the door 600 if desired.

In yet another embodiment of the invention, shown in FIGS. 10A and 10B, the securement component of the invention has been modified whereby the left and right adjustable reduction sleeves which were associated with the top securement brace have been eliminated and replaced with a frame support bracket 560. All components of frame support bracket 560 are constructed of the same materials as that of bondage frame 20 and it should be understood that all of the other top and bottom components that were previously described as forming a part of the securement are still incorporated into the securement of this embodiment. The frame support bracket 560 is designed to handle much heavier loads that may be placed on bondage frame 20 during use and this frame support bracket 560 is best depicted in FIG. 10B, where it is seen to be comprised of a left sub-bracket 562 and a right sub-bracket 582 and a removable stabilization bar 585 that attaches to and interconnects each sub-bracket together. Because the left and right sub-brackets are identical to each other, only the left sub-bracket 562 will be described in greater detail. In FIG. 10A, it is seen that the left sub-bracket 562 is comprised of a horizontal ledger 564, a vertical joist 570 and an angled joist 576, whereby the vertical joist and angled joist are integrally connected to the horizontal ledger. The horizontal ledger 564 is seen to have an open, first end 563 that is associated with the door 600 (not shown) and a second end 565 that is associated with the bondage frame 20. The first end 563 is provided with the set of holes 566a,566b that are diametrically across from each other in registered alignment. The diameter of the holes are matched to the holes 275a,b formed in the left securement arm 270 that is attached to the top securement brace 262 (see FIG. 3). Holes 566a and 566b are disposed the same distance away from end surface 567 as the holes 275a and 275b are disposed away from the proximate web outside surface 269t of top securement brace 262 (See FIG. 3) so that holes 566a,b and 275a,b align when the sub-bracket is attached to the left securement arm 270. After hole sets 566a,566b and 275a,275b are aligned for attachment purposes, a locking pin 500 is inserted through all holes, thereby securing and attaching the sub-bracket to the securement brace 262. The second end 565 of sub-bracket 562 is comprised of a horizontal reduction sleeve 568. This horizontal reduction sleeve is an exact copy of the horizontal reduction sleeve that was shown and described earlier as element 28 on the left stirrup assembly 24 of bondage frame 20, therefore, the components and component identifiers of element 28 will be used to describe the same elements on horizontal reduction sleeve 568. Horizontal reduction sleeve 568 includes an inside sleeve 120 that is provided with projecting tabs 46a,46b. When the left sub-bracket 562 is connected to bondage frame 20, the inside sleeve slid within the stub shaft 47 that is associated with the left stirrup assembly 24 on bondage frame 20 until the projecting tabs 46a,46b, engage the holes 52a,52 formed in the stub shaft 47 (See FIG. 3).

As mentioned above, the left sub-bracket 562 is also comprised of vertical joist 570 and an angled joist 576. The vertical joist 570 has a first end 572 that is integral with horizontal ledger 564 at end 563 and a second end 574 that is integral with a second end 584 of the angled joist 578. In the figures, it is seen that vertical joist 570 is also provided with a horizontal reduction sleeve 568 near second end 574, said horizontal reduction sleeve being the same as that provided on the horizontal ledger 564 and previously described. A similarly disposed horizontal reduction sleeve would also be provided on the right sub-bracket 582 as shown in FIG. 10B. The angled joist 576 is comprised of body portion having a first, upstanding end 582 that is integral with horizontal ledger 564 and a second, horizontal end 584 that is integral with the second end 574 of vertical joist 570.

The removable stabilizer bar 585 is very similar in construction to the lower cross link 240 that was previously described herein except that it is longer and of a length that will bridge the distance between the left and the right sub-brackets when interconnected thereto. As FIG. 10B best shows, stabilizer bar 585 has a first end 587 and a second end 589, with each end provided with identically-sized hole sets 590a,590b that are diametrically across from each other and which are in registered alignment with each other. The hole sets 590a,590b are located the same distance away from each respective end. Each respective hole set 590a,590b, is for receiving therein, a set of projecting tabs 46a,46b on the inside sleeves 120 that are associated with horizontal reduction sleeves 28 that are provided on each vertical joist of the left and right sub-brackets 562, 582 after the inside sleeves 120 are slid within the open tubular ends 587,589 of the stabilizer bar 585.

Now that all of the embodiments of the invention have been described, the full assembly of the bondage frame 20 to the securement means will now be described. First, an intended door must be opened enough to fully expose the top and bottom edges of the door. Then, the respective top and bottom securement braces 262,302, which each form a U-shaped channel, are slid along the top and bottom edges of the door until being centered along the respective edge. The U-shaped channel that is associated with the top of the door rests upon the top door edge such that the intermediate web 266 rests upon the top edge while the distal web 264 and proximate web 268 contact against the outside and inside faces of the door. The proximate web 268 should be associated with the side of the door that faces the inside of the room in which the restraining system is being assembled within. The bottom securement brace 302 would be slid along the bottom door edge in a similar fashion with the proximate web 308 of that brace facing the inside of the room. Sometimes, the thickness of a door will vary and should a thinner door be encountered, the securement braces will not be firmly held in place on the respective door edges such that the securement braces will tend to rock or wobble along the door edge. To account for such variations and ensure that the top and bottom securement braces 262,302 are firmly held in place on the door, it may be necessary to shim the braces if they are loose after initially placed on the door. To eliminate that problem, a simple shim system can be provided on each securement brace. The shim system is not shown in the drawing figures because those in the art would easily understand the concept and the components without the need to describe them in detail with the use of drawing figures. The shim system would be comprised of a first strip of Velcro material being attached with double stick tape to the respective inside surfaces 269i,309i on the proximate web 268,308 of each securement brace 262,302. An elongate strip of wood or other suitable materials would be provided which is covered with the mated Velcro material to that which is already attached to the proximate web. The elongate strip should be no thicker than ⅜" prior to the Velcro being attached to it and said strip should be made substantially the same length as the securement brace. The elongate strip is to be attached to the Velcro strip inside the securement brace prior to the respective braces being re-installed on the door edges. The shim system can be readily removed if need be upon the next assembly of the restraint system on a different door, unless the same door is going to be used upon the next assembly. In either case, the left and right short adjustable reduction sleeves 284a,284b are then connected to the left and right securement arms 270,276, as previously described herein above. The left and right modified, short adjustable reduction sleeves 334a,334b, are then connected to the left and right stanchions 310,320, as previously described herein above. The bondage frame 20 is then assembled by connecting the left and the right upper stirrup assemblies to the upper center link 70 or to each other if the upper cross link member shown in FIG. 9A is employed. Each of the vertical posts 80, 150 are then attached to the upper cross member 22, whereby left post 80 connects to the downward reduction sleeve 27 and right post 150 connects to the downward reduction sleeve 57. Next, the bottom cross member 200 is assembled by connecting the lower left and lower right stirrup assemblies to the lower cross link 240 or to each other if the lower cross link member shown in FIG. 9B is employed. The top and bottom cross members should be matched so if one is assembled with the center link, then the other should be also. Once the frame 20 is fully assembled, the stub shafts 47,67,210,230, that are associated on each of the stirrup assemblies are then connected to the short, adjustable reduction sleeves and to the modified, short adjustable reduction sleeves 284a,284b, 334a,334b. If it is determined that the frame should extend further away from the door, then the short and modified short adjustable reduction sleeves would be adjusted accordingly. Likewise, if the frame was determined to need adjustment in the vertical direction to make the frame shorter or longer, the tall, adjustable reduction sleeves on each of the vertical posts would be adjusted accordingly.

Operational implementation of the restraining system of the invention is left to the needs and/or the imagination of the Dom exercising the power and control over the slave. In FIG. 1, it is seen that the restraints that are being employed in this illustration are both the adjustable wrist restraining cuffs 400a and the adjustable ankle restraining cuffs 400b. As mentioned earlier herein, other restraints could be used in place of in addition to the limb restraining cuffs such as a bondage collar or bondage belt, etc. In FIGS. 5A and 5B is seen that the restraining cuffs may be provided with either a conventional buckle for adjusting the size and tightness the attachment of the cuffs about the wrists and ankles or preferably, they may be provided with a Velcro material. With either choice, these drawing figures illustrate that each cuff is manufactured with an attachment loop 401. This loop is either made by slitting the cuff material or it is made from a separate piece of material that is either sewn onto the cuff or is attached by other means such as gluing and heat bonding. The loop 401 receives a permanent attachment ring 402 that is used for connecting the cuffs to various types of restraint assistors 450. In FIG. 5A, attachment ring 402 is seen connected to spring-loaded restraint assistors identified herein as a round eye swivel quick snap connector 458a, while in FIG. 5B, the attachment ring 402 is connected to a spring link connector 456. FIG. 4 shows another type of spring loaded restraint assistor identified herein as a round eye swivel tie snap connector 458b which may also be attached to the restraint cuffs by way of the attachment ring 402. Each type of spring-loaded swivel type of connector 458a and 458b has a respective open swiveling hook portion 459a,459b, a spring-loaded catch portion 460a,460b that closes the hook portion, and an eye portion 461a,461b for connecting the swivel connector to another component. The catch portions 461a,461b of each type of swivel connector would be moved to fully expose the hook portions 459a, 459b so that an attachment ring 402 can be looped into engagement about the hook portions prior to the catch portions being released. The respective eye portions 460a, 460b are typically connected to another restraint assistors such as a mounting ring 462, as best seen in FIG. 1. The restraint system anticipates various types of restraint assistors being used to promote a particular restraining function. For example, the spring link connector 456 promotes a quick and efficient means of directly or indirectly connecting and disconnecting the restraining cuffs to the bondage frame 20. As FIG. 1 shows, all of the cuffs 400a,400b are attached to a spring link connectors 456 via the cuff attachment rings 402, while the snap connector is also connected to a respective mounting ring 462. The mounting rings 462 are identical and they are of the split ring type that is commonly used with key chains, only larger, with each one permanently secured about a respective stirrup segment. On the upper stirrup assemblies 24,54, mounting rings 462 are mounted about respective segments 26c,26d and 56c,56d, while on the lower stirrup assemblies 202,222, the mounting rings 462 are secured about segments 204c and 224c. The mounting rings 462 themselves provide an expedient and efficient manner of attaching a chosen restraint or a chosen restraint assistors to the bondage frame. If the mounting rings 462 were not provided, it would be impossible to mount a spring link connector or either type of the spring-loaded swivel connectors directly to the frame since the frame tubing diameter is larger than the eye portions of the swivel connectors and any opening that a spring link connector presents. Furthermore, without the provision of mounting rings 462, there would not be an efficient way of connecting the attachment ring 402 of restraint 400 to bondage frame 20 short of tying the attachment ring 402 to the frame with either rope, wire or electrical wire ties. Connecting any restraint 400 to directly to bondage frame 20 is not desirable because it restricts the usage of the restraint 400 to only that portion of the frame. For example, if the ankle cuffs 400b were directly connected to the respective segments 202c, 222c of the lower left and lower right stirrup assemblies 202, 222, the adaptability of the bondage frame for use with other types of restraints for various creative functions would be stifled because only restraining cuffs could be used at that location. Therefore, it should be appreciated that whenever a restraint assistors or one of the restraints itself is going to be attached to any one of the stirrup assemblies 24,54,202, or 222, a mounting ring 462 is preferably required. However, mounting rings 462 may not necessarily be required when a restraint assistors or the chosen restraint itself is going to be attached to any other part of bondage frame 20. For example, in FIGS. 1 and 4, it is seen that upper center link 70 includes two types of restraint assistors, a tie-down cleat 452 and a matched pair of attachment brackets 451. The attachment brackets 451 each have a spring link connector 456 directly attached thereto instead of a mounting ring 462, which means at this frame location, some of the restraint assistors can be directed attached to bondage frame 20. The spring link connectors 456 are seen to be further connected to the eye portions 460b of an adjustment pulley, yet another type of restraint assistors, although the spring link connector could have been directly connected to attachment ring 402 on wrist cuff 400a, although as already mentioned above, it is not desirable to directly attach the restraints to bondage frame 20. Restraint assistors 450 in the form of adjustment pulleys 466 may be incorporated at various locations about bondage frame 20 and they may be single-spooled pulleys 466 or they can be multi-spooled pulleys. In FIG. 1, single-spooled pulleys are being utilized with wrist cuffs 400a, while in FIG. 4, it is seen that a pair of double-spooled pulleys 468 are associated with the each of the attachment brackets 451. The tie-down cleats 452 shown in FIGS. 1 and 4 represent still another type of restraint assistors, as do the bondage ropes 490 that are only shown in FIG. 1. It is envisioned that with double-spooled pulleys, several bondage ropes can be simultaneously used by the Dom and the invention is not to be so limited to only using the bondage ropes 490 shown in FIG. 1 and only at that location. The two bondage ropes 490 shown in FIG. 1 are identical, each having a free end 491 and a closed, looped end 492 and any such additional bondage ropes that may be utilized by a Dom with the present restraint system will have the same construction. The looped end 492 will always be attached to a chosen restraint and in FIG. 1, it is clear that restraint of choice here are the wrist cuffs 400a. However, it should be understood that the looped end 492 could instead be attached to other types of restraints such as a bondage bar, bondage restraining collar, or bondage belt, etc., (each not shown) and wherein the respective free ends 491 could be directly attached to a tie-down cleat 452 on the vertical posts 80,150, or to the tie-down cleat 452 on the top cross link 70, depending upon what type of restraint 400 is selected by the Dom and what position the Dom desires to retrain his slave. Alternatively, and as FIG. 1 supports, the free ends 491 of bondage ropes 490 could be indirectly attached to bondage frame 20 by first coupling them with another type of restraint assistors, here single-spooled adjustment pulleys 466. With this combination of restraint (wrist cuffs) and restraint assistors (ropes, pulleys, tie-down cleats), the wrists of the slave can be restricted so as to create a wrists-offered position if the slave is facing the bondage frame or a strappado position if the slave is facing away from the bondage frame. If the wrists cuffs were instead arranged just above the elbows rather than at the wrists, and the slave was facing away from the door, the arms of the slave could be pulled in a backwards direction towards the door into a waitress position. Moreover, instead of one of those specific and known bondage positions, a Dom could simply bind the wrists of his slave with wrist cuffs and tighten the bondage ropes by pulling on the free ends until the wrists, and hence the arms, of the slave are raised above or at the head-level of the slave, depending upon how tall the slave is. This raised arms position would be maintained by securing the free ends of the bondage ropes 490 about the tie-down cleats 452 on vertical posts 80,150 or cleat 452, as shown in FIG. 1, or if the double-spooled pulleys shown in FIG. 4 were instead implemented, the free ends 491 could be secured to the tie-down cleat 452 on upper cross link 70. Moreover, if the second embodiment of the upper cross member 22' (FIG. 9A) was being used as part of bondage frame 20, then either or both of the tie-down cleats 452 on each upper stirrup assembly could be utilized to secure the free ends 491. In carrying out the invention, it should be appreciated that a variety of restraining devices and restraint assistors may be implemented with bondage frame 20 to create an almost limitless number of positions and methods for restraining a human slave.

While the apparatus and methods described herein form a preferred embodiment of this invention, it is evident that many alternatives, modifications, and variations will be apparent to those skilled in the art in light of the foregoing description. Accordingly, it will be understood that this invention is not so limited, and changes can be made without departing from the scope and spirit of this invention, which is defined in the appended claims.

I claim:

1. A portable human restraint system for selectively limiting movement of at least one part of the human body for use by those who practice an alternative sexual lifestyle known as dominance and submission or discipline and bondage, the restraint system intended for use inside a room that is provided with a door having a top and a bottom edge, the restraint system comprising:

a readily dismantled bondage frame having at least a part thereof continuously resting upon the floor surface of the room;

a securement that secures the bondage frame to the top and bottom edge surfaces of the door, the securement comprised of top and bottom securement brace, each securement brace having a generally U-shaped construction defined by respective interconnected distal, intermediate, and proximate webs, and wherein the webs of the top securement brace envelope the top edge surface of the door and the webs of the bottom securement brace envelope the bottom edge surface of the door;

the securement further comprising a pair of securement arms attached to the top securement brace and a pair of stanchions attached to the bottom securement brace, wherein each securement arm has a corresponding first and second end and each stanchion has a corresponding top and bottom end, wherein the first ends of the securement arm are attached to the proximate web of the top securement brace and the bottom ends of the stanchions are attached to a respective stanchion plate, each of the stanchion plates attached to the proximate web of the bottom securement brace;

the securement further includes a left and a right short, adjustable reduction sleeve, the left short, adjustable reduction sleeve associated with the left securement arm and the right short, adjustable reduction sleeve associated with the right securement arm, each of the short, adjustable reduction sleeves having respective and corresponding first and second ends connected to a respective stub shaft on the left and right horizontal reduction sleeves, wherein the respective first ends are connected to the second ends of each of the securement arms and the respective second ends are connected to the bondage frame;

upper left and upper right stirrup assemblies connected to the short, adjustable reduction sleeves, each of the short, adjustable reduction sleeves is extendable such that the upper left and upper right stirrup assemblies can be moved in a direction away from the door;

a restraint that is adapted to selectively restrain movement of at least one part of the human body relative to the bondage frame; and a plurality of restraint assistors disposed about the bondage frame, restraint assistors adapted to cooperate with the non-elastic restraint to effectuate restraint of the at least one part of the human body.

2. The restraint system of claim 1, wherein the securement is comprised of an identical top and bottom securement brace.

3. The restraint system of claim 2, wherein the securement further includes a pair of identical securement arms attached to the top securement brace and a pair of identical stanchions attached to the bottom securement brace.

4. The restraint system of claim 3, wherein the securement further includes an identical left and a right short, adjustable reduction sleeve.

5. The restraint system of claim 4, wherein the securement further includes an identical left and a right modified, short adjustable reduction sleeve associated with the bottom securement brace, each of the modified, short, adjustable reduction sleeves having respective and corresponding first and second ends.

6. The restraint system of claim 5, wherein the first ends of each of the modified, short, adjustable reduction sleeves are connected to respective the top ends of the stanchions and the second ends of each of the modified, short, adjustable reduction sleeves are connected to the bondage frame.

7. The restraint system of claim 6, wherein the second end of each of the modified short, adjustable reduction sleeves is connected to a respective stub shaft on the lower left and lower right horizontal reduction sleeves.

8. The restraint system of claim 7, wherein each of the modified short, adjustable reduction sleeves is extendable such that the lower left and lower right stirrup assemblies can be moved in a direction away from the door.

9. The restraint system of claim 8, wherein the bondage frame is comprised of a top cross member, a bottom cross member, a left vertical post and an identical right vertical post, the top and bottom cross members being disposed in a parallel relationship to the other and the left and right vertical posts being disposed in a parallel relationship to the other, wherein each of the vertical posts are interconnected to the top and bottom cross members such that the bondage frame has a generally rectangular configuration.

10. The restraint system of claim 9, wherein the top cross member is comprised of an upper left stirrup assembly and an identical upper right stirrup assembly, each of the left and right stirrup assemblies including respective top, bottom and side stirrup segments that are integrally connected together so as to form a generally square configuration and a respective upper left stirrup opening and an upper right stirrup opening.

11. The restraint system of claim 10, wherein the top stirrup segments of the upper left and upper right stirrup assemblies have a respective horizontal reduction sleeve integrally formed therein, wherein the horizontal reduction sleeve on the left stirrup assembly horizontally extends towards the right stirrup assembly and the horizontal reduction sleeve on the right stirrup assembly horizontally extends towards the left stirrup assembly such that each of the horizontal reduction sleeves are in registered alignment with the other and wherein the bottom stirrup segments on each of the upper left and upper right stirrup assemblies have a respective downward reduction sleeve integrally formed therein, wherein the downward reduction sleeves extend downwardly towards a respective left and right vertical post such that each of the downward reduction sleeves are in registered alignment with a respective vertical post.

12. The restraint system of claim 11, wherein the downward reduction sleeve on the left stirrup assembly connects to a top end of the left vertical post and the downward reduction sleeve on the right stirrup assembly connects to a top end of the right vertical post.

13. The restraint system of claim 12, wherein the bottom cross member is comprised of a lower left stirrup assembly and an identical lower right stirrup assembly, each of the lower left and lower right stirrup assemblies including respective top, bottom and side stirrup segments that are integrally connected together so as to form a generally rectangular configuration and a respective lower left stirrup opening and a lower right stirrup opening.

14. The restraint system of claim 1, wherein the top stirrup segments on each of the lower left and lower right stirrup assemblies have a respective horizontal reduction sleeve integrally formed therein, the horizontal reduction sleeve on the lower left stirrup assembly horizontally extending towards the lower right stirrup assembly and the horizontal reduction sleeve on the lower right stirrup assembly extending horizontally towards the lower left stirrup assembly such that each of the horizontal reduction sleeves are in registered alignment with the other and wherein the bottom segments on each the lower left and upper right stirrup assemblies has a respective upward reduction sleeve integrally formed therein such that the respective upward reduction sleeves extends upwardly and in registered alignment with a respective left and right vertical post.

15. The restraint system of claim 14, wherein the upward reduction sleeve on the lower left stirrup assembly connects to a bottom end of the left vertical post and the upward reduction sleeve on the lower right stirrup assembly connects to a bottom end of the right vertical post.

16. The restraint system of claim 15, wherein the horizontal reduction sleeves on each of the upper left and upper right stirrup assemblies are directly fastened together and the horizontal reduction sleeves on each of the lower left and lower right stirrup assemblies are directly fastened together.

17. The restraint system of claim 16, wherein the horizontal reduction sleeves on each of the upper left and upper right stirrup assemblies are indirectly fastened together through an upper cross link that extends between the upper stirrup assemblies and wherein the lower left and lower right stirrup assemblies are indirectly fastened together through a lower cross link that extends between the lower stirrup assemblies.

18. The restraint system of claim 17, wherein each of the short adjustable reduction sleeves are connected to the top securement brace through a removable connection and wherein each of the modified short, adjustable reduction sleeves are connected to the bottom securement brace through a removable connection, wherein each of the connections are identical to the other, and wherein the connection is comprised of one of a wire lock pin, a clevis pin, and a combination of a nut and a bolt.

19. The restraint system of claim 18, wherein the left and right vertical posts are identical to each other, wherein each of the posts is comprised of a respective top and bottom section, wherein each of the top sections are comprised of a tubular member and each of the bottom sections are comprised of a tall, adjustable reduction sleeve.

20. The restraint system of claim 19, wherein each of the tall, adjustable reduction sleeves is expandable in a vertical direction such that a height of the bondage frame can be lengthened.

21. The restraint system of claim 20, wherein the top cross member and the bottom cross member and each of the vertical posts include a combination of respective restraint assistors for directly connecting a non-elastic restraint to the bondage frame, the combination comprising one of a tie-down cleat, a mounting ring, and an attachment bracket.

22. The restraint system of claim 21, wherein the top cross member and the bottom cross member and each of the vertical posts include a combination of respective restraint assistors for indirectly connecting a non-elastic restraint to the bondage frame, the combination comprising one of an adjustment pulley, a spring link, a round eye swivel quick snap and a round eye swivel tie snap.

23. The restraint system of claim 22, wherein the non-elastic restraint is comprised of one of a bondage restraining collar, a bondage belt, a spreader bar, a restraining harness and at least one pair of limb restraining cuffs.

24. A portable human restraint system for selectively limiting movement of at least one part of the human body for use by those who practice an alternative sexual lifestyle known as dominance and submission or discipline and bondage, the restraint system intended for use inside a room that is provided with a door having a top and a bottom edge, the restraint system comprising:

the restraint system intended for use inside a room that is provided with a door having a top and a bottom edge, the restraint system comprising:

a readily dismantled bondage frame;

a securement that secures the bondage frame to the top and bottom edges of the door, the securement comprised of top and bottom securement brace, each securement brace having a generally U-shaped construction defined by respective interconnected distal, intermediate, and proximate webs, and wherein the webs of the top securement brace envelope the top edge surface of the door and the webs of the bottom securement brace envelope the bottom edge surface of the door;

the securement further comprising a pair of securement arms attached to the top securement brace and a pair of stanchions attached to the bottom securement brace, wherein each securement arm has a corresponding first and second end and each stanchion has a corresponding top and bottom end, wherein the first ends of the securement arm are attached to the proximate web of the top securement brace and the bottom ends of the stanchions are attached to a respective stanchion plate, each of the stanchion plates attached to the proximate web of the bottom securement brace;

the securement further includes a left and a right short, adjustable reduction sleeve, the left short, adjustable reduction sleeve associated with the left securement arm and the right short, adjustable reduction sleeve associated with the right securement arm, each of the short, adjustable reduction sleeves having respective and corresponding first and second ends, wherein the respective first ends are connected to the second ends of each of the securement arms and the respective second ends are connected to the bondage frame;

the securement further includes a removable frame support bracket interposed between and simultaneously connected to the top securement brace and the bondage frame, the frame support bracket comprised of a left and a right sub-bracket and a stabilization bar, the stabilization bar extending between each of the sub-brackets and removably connected thereto;

a restraint that is adapted to selectively restrain movement of at least one part of the human body relative to the bondage frame; and a plurality of restraint assistors disposed about the bondage frame, the restraint assistors adapted to cooperate with the non-elastic restraint to effectuate restraint of the at least one part of the human body.

25. The restraint system of claim 24, wherein the securement is comprised of an identical top and bottom securement brace.

26. The restraint system of claim 25, wherein the securement further includes a pair of identical securement arms attached to the top securement brace and a pair of identical stanchions attached to the bottom securement brace.

27. The restraint system of claim 26, wherein the securement further includes an identical left and a right modified, short adjustable reduction sleeve associated with the bottom securement brace.

28. The restraint system of claim 24, wherein the frame support bracket is comprised of an identical left and right sub-bracket and a stabilization bar, the stabilization bar extending between each of the sub-brackets and removably connected thereto.

29. The restraint system of claim 28, wherein each of the identical sub-brackets is comprised of a horizontal ledger, a vertical joist and an angled joist, the horizontal ledger having a first and a second end, the vertical joist having a first and a second end and the angled joist having a first and a second end, wherein the first end of the vertical joist is integrally connected to the first end of the horizontal ledger and the first end of the angled joist is integrally connected near a second end of the horizontal ledger and the second end of the angled joist is integrally connected to the second end of the vertical joist, wherein the first ends of each of the horizontal ledgers presents a respective opening that receives therein a respective the securement arm of the top securement and wherein the second end of each of the horizontal ledgers is comprised of a respective and identical reduction sleeve, which the identical reduction sleeves are removably attached to the bondage frame.

* * * * *